(12) United States Patent
Williams

(10) Patent No.: US 12,171,280 B1
(45) Date of Patent: Dec. 24, 2024

(54) COMFORTABLE ABSORBENT BRA

(71) Applicant: Mosezella Williams, Stuart, FL (US)

(72) Inventor: Mosezella Williams, Stuart, FL (US)

(*) Notice: Subject to any disclaimer, the term of this patent is extended or adjusted under 35 U.S.C. 154(b) by 95 days.

(21) Appl. No.: 17/991,313

(22) Filed: Nov. 21, 2022

(51) Int. Cl.
*A41C 3/12* (2006.01)
*A61F 13/15* (2006.01)

(52) U.S. Cl.
CPC ...... *A41C 3/12* (2013.01); *A61F 2013/15016* (2013.01)

(58) Field of Classification Search
CPC .................................................. A41C 3/12
USPC ............................................................ 450/89
See application file for complete search history.

(56) References Cited

U.S. PATENT DOCUMENTS

| | | | | |
|---|---|---|---|---|
| 1,904,344 A * | 4/1933 | Andrews | .......... | D01H 5/64 15/256.51 |
| 2,497,324 A * | 2/1950 | Schenkman | .......... | A41C 3/0021 2/338 |
| 2,773,261 A * | 12/1956 | Schaumer | .......... | A41C 3/00 450/86 |
| 2,802,213 A * | 8/1957 | Rosenthal | .......... | A41C 3/0021 450/60 |
| 3,698,399 A * | 10/1972 | Hand | .......... | A41C 3/0021 450/59 |
| 4,295,469 A * | 10/1981 | Lindgren | .......... | A41C 3/142 450/61 |
| 7,214,120 B2 | 5/2007 | Kaye et al. | | |
| 10,104,919 B2 | 10/2018 | Perl | | |
| 2013/0122780 A1 * | 5/2013 | McCall | .......... | A41C 3/10 450/36 |

* cited by examiner

*Primary Examiner* — Gloria M Hale

(74) *Attorney, Agent, or Firm* — Sanchelima & Associates, P.A.; Christian Sanchelima; Jesus Sanchelima

(57) ABSTRACT

A comfortable absorbent bra including a brassiere assembly, a pocket assembly, and a laces assembly. Brassiere assembly includes a first cup and a second cup. The first cup and second cup have a shape that is in contact with the shape of the woman's breast. The first cup and second cup are held in place through a bridge and backstraps included in laces assembly. Pocket assembly includes a first pocket and a second pocket. First pocket and second pocket have a half-circle shape with a concave portion. A portion of the periphery of first pocket and second pocket are attached to an internal portion of the first cup and second cup respectively creating a receiving portion for the woman's breast.

9 Claims, 3 Drawing Sheets

COMFORTABLE ABSORBENT BRA

II. BACKGROUND OF THE INVENTION

1. Field of the Invention

The present invention relates to a brassiere and, more particularly, to a comfortable absorbent bra that includes a pocket in an internal area on each cup giving support eliminating skin to skin contact and preventing perspiration.

2. Description of the Related Art

Several designs for brassieres have been designed in the past. None of them, however, include a pocket attached on an internal side of a bra, wherein the pocket has a receiving portion for the woman's breast, providing comfort and preventing perspiration.

Applicant believes that a related reference corresponds to U.S. Pat. No. 10,104,919 issued for bra lining. Applicant believes that another related reference corresponds to U.S. Pat. No. 7,214,120 issued for brassiere having spacer fabric and a method of making the same. None of these references, however, teach of a brassiere formed with cups that include an absorbent padding.

Other documents describing the closest subject matter provide for a number of more or less complicated features that fail to solve the problem in an efficient and economical way. None of these patents suggest the novel features of the present invention.

III. SUMMARY OF THE INVENTION

It is one of the objects of the present invention to provide a bottom cup depth shape pocket that comfort, lift shape and support women's breasts.

It is another object of this invention to provide a shape pocket inside a brassiere to eliminate skin to skin contact and to prevent discomfort caused by perspiration.

It is still another object of the present invention to provide a stylish brassiere to provide a more attractive feminine look.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

IV. BRIEF DESCRIPTION OF THE DRAWINGS

Figure 1:
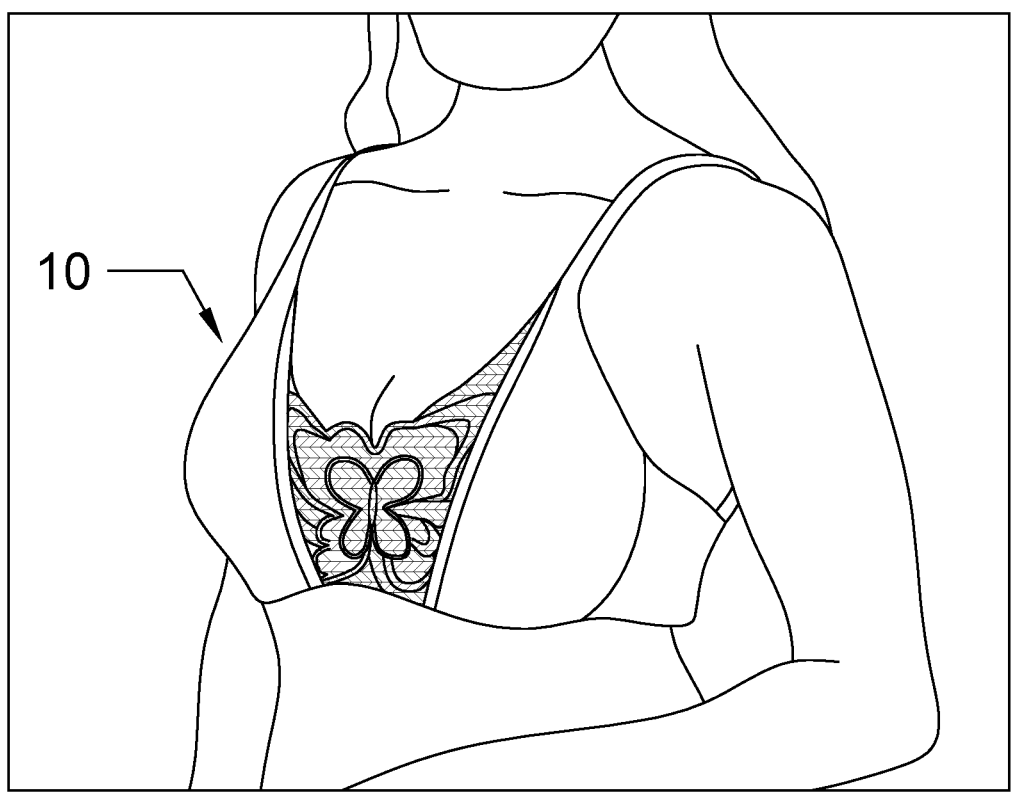

With the above and other related objects in view, the invention consists in the details of construction and combination of parts as will be more fully understood from the following description, when read in conjunction with the accompanying drawings in which:

FIG. 1 represents an operational view of an exemplary embodiment of the present invention 10.

Figure 2:
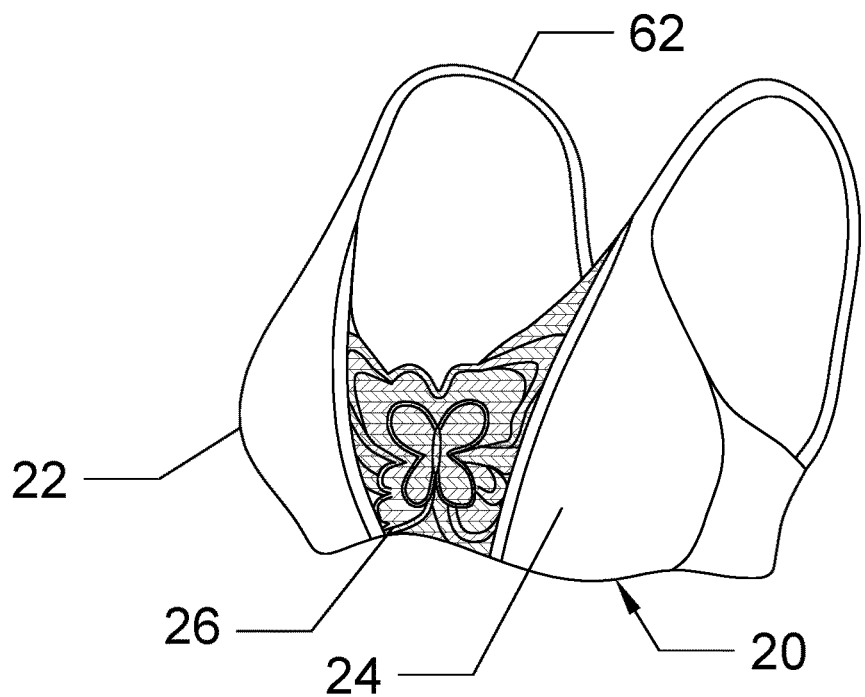

FIG. 2 shows an isometric view of the present invention 10, wherein the bridge 64 has a butterfly-shaped to join the first cup 22 and the second cup 24.

Figure 3:
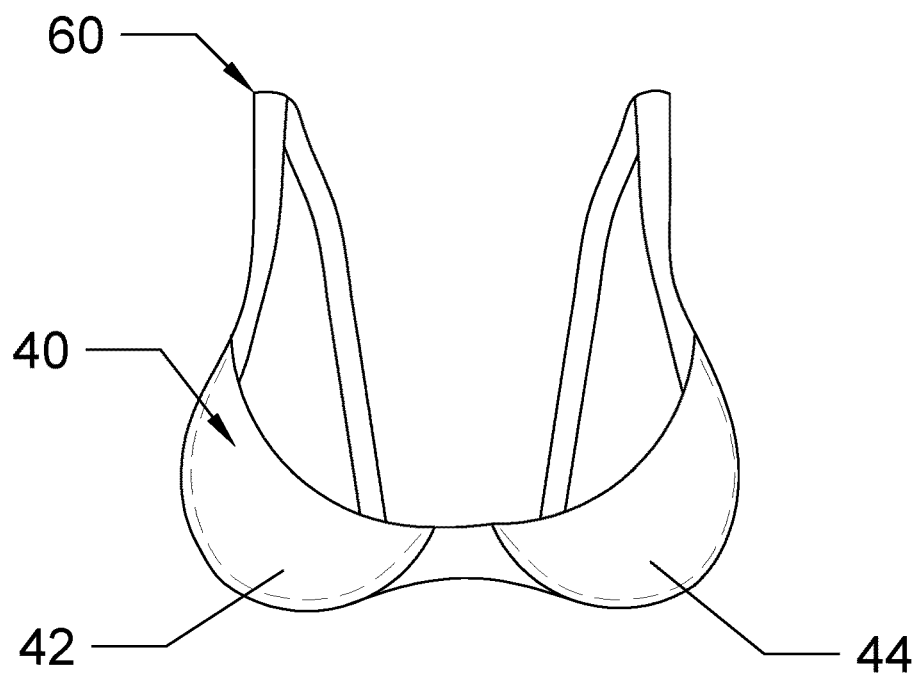

FIG. 3 illustrates a front cross-section view of the present invention 10, where the first pocket 42 and the second pocket 44 are attached in a back side of the brassiere assembly 20.

Figure 4:
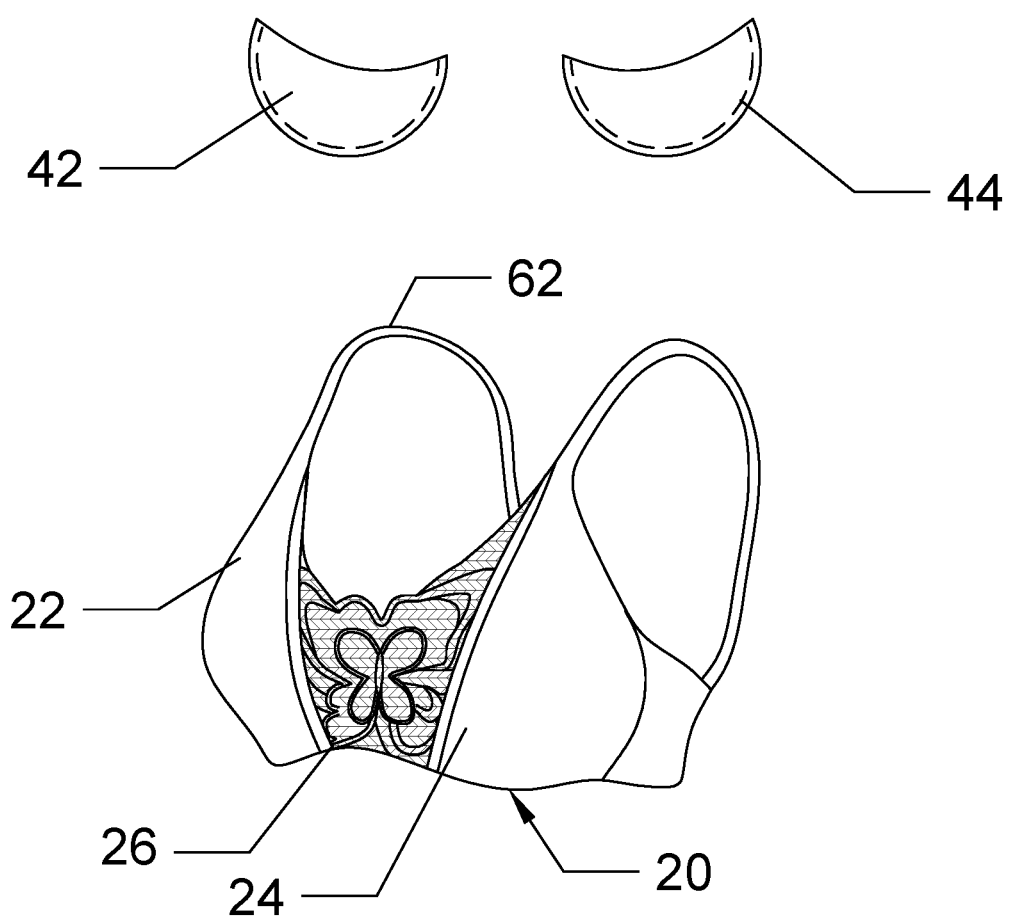

FIG. 4 is a representation of an exploded of a suitable embodiment of the present invention 10, wherein the half-circle shape of the pocket assembly 40 is attached to a back side periphery of the brassiere assembly 20, creating a receiving portion between the brassiere assembly 20 and the pocket assembly 40.

V. DETAILED DESCRIPTION OF THE EMBODIMENTS OF THE INVENTION

Referring now to the drawings, where the present invention is generally referred to with numeral 10, it can be observed that it basically includes a brassiere assembly 20, a pocket assembly 40 and laces assembly 60. It should be understood there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

Brassiere assembly 20 includes a first cup 22 and a second cup 24, wherein the first 22 cup and second cup 24 may be elements of a brassiere well known in prior art. In an exemplary embodiment first cup 22 and second cup 24 may be elements of a push up bra, a padded bra, a t-shirt bra, or any other variation thereof. In a preferred embodiment, first cup 22 and second cup 24 are made of a tricot material, a spandex material, a satin material, a cotton material, polyester, or any other suitable materials for brassieres. It should be considered that first cup 22 and second cup 24 may be attached to the band that is configure to wrap around the user's body, wherein first cup 22 and second cup 24 may be configured to fit the user's breast, nonetheless, it should be considered that a pre-molded foam cup may be attached to the attached to the internal area that conforms the first cup 22 and second cup 24. Brassiere assembly 20 further includes a bridge 26, wherein the bridge 26 may be the center area between first cup 22 and second cup 24. In a suitable embodiment, bridge 26 may be configured to provide separation of the user's breast, putting the user's breast in proper position to ease into first cup 22 and second cup 24. It should be considered that bridge 26 may have a flat surface between the first cup 22 and second cup 24, nevertheless, a predetermined design may be included on the external surface of the bridge 26, wherein the predetermined design may be included on a front portion of first cup 22 and second cup 24, thereby the predetermined design may provide an attractive user look. As best depicted in FIG. 1.

Pocket assembly 40 includes a first pocket 42 and a second pocket 44, wherein first pocket 42 and a second pocket 44 are attached in a rear side of first cup 22 and second cup 24 respectively. As shown in FIG. 4. In an exemplary embodiment, first pocket 42 and a second pocket 44 may have a half-circle shape with a concave portion. As illustrated in FIG. 4. In a suitable embodiment, a portion of the periphery that conforms the half-circle shape of first pocket 42 and the second pocket 44 is attached to a portion of the periphery of first cup 22 and second cup 24, wherein the concave portion that is not attached to the first cup 22 and second cup 24 creates an opening, thereby a receiving portion is created between first cup 22 and the second cup 24 with respect to first pocket 42 and second pocket 44 respectively. In a preferred embodiment, first pocket 42 and second pocket 44 may be made of a tricot material, a spandex material, a satin material, a cotton material, polyester or any other suitable material that prevents perspiration.

Laces assembly 60 includes a backstrap, wherein the backstraps includes straps attached to a portion of each of first cup 22 and second cup 24 that are configured to go up and over the user's shoulder and join to the back of the brassiere. Best illustrated in FIG. 2. In one embodiment, backstrap 60 may be made of an elastic material, wherein said straps that conforms the backstrap 60 may be adjusted in a preferred length by the user. It should be considered that backstrap 60 may include a padding material that is configured to be in contact with the user. Backstrap 60 in other embodiment may conform one element with the back of the brassiere. In a suitable embodiment, backstrap is configured to hold the first cup 22 and second cup 24 in a proper position on the user's body.

Referring to FIG. 3, pocket assembly 60 is configured to be in contact with the skin of the user's body, wherein the user's breast may be placed into the receiving portion created between brassiere assembly 20 and pocket assembly 60, thereby the present invention 10 may provide shape and support for the user's breast while backstrap is adapted to the user's shoulders. As best depicted in FIG. 1. Nonetheless, in other embodiment of the present invention 10, laces assembly 60 may be not included, thereby the back of the brassiere is adapted to round the user's body providing most of the brassiere support, wherein the back of the brassiere may be made of an elastic material and may be attached to itself by means of fasteners placed at the edges that conforms the back of the brassiere. It should be considered that the present invention 10 may include indicia of a brand in a portion thereof.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An absorbent bra, comprising:
   a brassiere assembly including a first cup and a second cup, wherein said brassiere assembly further includes a bridge, said bridge attached between said first cup and said second cup, said bridge is in a central front area of said brassiere assembly, wherein said brassiere assembly is made of cotton, wherein a bottom end of said bridge has a length smaller than a length of a top end of said bridge defining a tapered shape wherein said bridge extends an area of at least a third of a total area of a front face of said brassiere assembly, said front face including said bridge, said first cup and said second cup;
   a pocket assembly having a first pocket and a second pocket, wherein said first pocket and said second pocket are attached to a rear side of said first cup and said second cup; and
   laces assembly including a backstrap, wherein said backstrap includes straps attached on a portion of said first cup and said second cup.

2. The absorbent bra of claim 1, wherein said bridge has a flat body.

3. The absorbent bra of claim 1, wherein a predetermined design is included in a front portion of said first cup and said second cup.

4. The absorbent bra of claim 1, wherein said first and said second pocket have a half-circle shape with a concave portion.

5. The absorbent bra of claim 4, wherein a circumference of said first pocket that conforms a periphery of said half-circle shape is attached to a periphery of said rear side of said first cup.

6. The absorbent bra of claim 4, wherein a circumference of said second pocket that conforms a periphery of said half-circle shape is attached to a periphery of said rear side of said second cup.

7. The absorbent bra of claim 1, wherein said first pocket and said second pocket attached to said first cup and said second cup respectively create a receiving portion.

8. The absorbent bra of claim 1, wherein said receiving portion is adapted to receive a user's breast.

9. A absorbent bra, consisting of:
   a brassiere assembly including a first cup and a second cup, wherein said first cup and said second cup has a shape that is configured to fit with a shape of a women's breast, said first cup and said second cup are configured to support said women's breast, said brassiere assembly further includes a bridge, said bridge is attached between said first cup and said second cup, said bridge has a predetermined design, wherein said predetermined design extends past to a portion of said first cup and said second cup, wherein said brassiere assembly is made of cotton, wherein a bottom end of said bridge has a length smaller than a length of a top end of said bridge defining a tapered shape, wherein said bridge extends an area of at least a third of a total area of a front face of said brassiere assembly, said front face including said bridge, said first cup and said second cup;
   a pocket assembly having a first pocket and a second pocket, wherein said first pocket has a half-circle shape with a concave portion, wherein said second pocket has a symmetrical shape with respect to said first pocket, wherein said first pocket and said second pocket are placed in an internal portion of said first cup and said second cup respectively, a portion of a circumference that conforms to the half-circle shape of said first pocket and said second pocket is attached to a rear periphery portion of said first cup and said second cup respectively, a receiving portion is created between said first and said second cup with respect to said first pocket and said second pocket respectively, said receiving portion is adapted to receive a user's breast; and
   a laces assembly including a backstrap and a bridge, wherein said backstrap includes a strap attached to said first cup and said second cup, said backstrap is adapted to be adjusted to a user's shoulder, said backstrap provides support to the brassiere assembly.

* * * * *